(12) United States Patent
Yang et al.

(10) Patent No.: US 11,492,376 B2
(45) Date of Patent: Nov. 8, 2022

(54) TOXOPLASMA GONDII GRA8-DERIVED RECOMBINANT PEPTIDES AND COMPOSITION FOR PREVENTING OR TREATING CANCER COMPRISING THE SAME

(71) Applicant: Industry—University Cooperation Foundation Hanyang University Erica Campus, Incheon (KR)

(72) Inventors: Chul-Su Yang, Ansan-si (KR); Jae-Sung Kim, Suwon-si (KR)

(73) Assignee: Industry-University Cooperation Foundation Ranyang University Erica Campus, Incheon (KR)

( * ) Notice: Subject to any disclaimer, the term of this patent is extended or adjusted under 35 U.S.C. 154(b) by 0 days.

(21) Appl. No.: 17/130,475

(22) Filed: Dec. 22, 2020

(65) Prior Publication Data
US 2021/0188916 A1    Jun. 24, 2021

(30) Foreign Application Priority Data

Dec. 24, 2019  (KR) .................. 10-2019-0174088
Aug. 11, 2020  (KR) .................. 10-2020-0100721

(51) Int. Cl.
| | | |
|---|---|---|
| C07K 14/00 | (2006.01) | |
| A61P 35/00 | (2006.01) | |
| A23L 33/00 | (2016.01) | |
| A23L 33/18 | (2016.01) | |
| A61K 38/00 | (2006.01) | |

(52) U.S. Cl.
CPC .............. *C07K 14/00* (2013.01); *A23L 33/18* (2016.08); *A23L 33/40* (2016.08); *A61P 35/00* (2018.01); *A23V 2002/00* (2013.01); *A61K 38/00* (2013.01)

(58) Field of Classification Search
None
See application file for complete search history.

(56) References Cited

FOREIGN PATENT DOCUMENTS

KR    10-2019-0059389    5/2019

OTHER PUBLICATIONS

Kim et al. "Toxoplasma gondii GRA8-derived peptide immunotherapy improves tumor targeting of colorectal cancer" Oncotarget 11: 62-73. (Year: 2020).*
Nguyen et al. "A Novel Soluble Peptide with pH-Responsive Membrane Insertion" Biochemistry 54:6567-6575. (Year: 2015).*
Kim et al. "Toxoplasma Gondii GRA8 Induces ATP5A1-SIRT3-Mediated Mitochondrial Metabolic Resuscitation: A Potential Therapy for Sepsis", Experimental & Molecular Medicine, 50(3): e464-1-e464-11, Published Online Mar. 30, 2018.

* cited by examiner

*Primary Examiner* — Sudhakar Katakam
*Assistant Examiner* — Zachary J Miknis

(57) ABSTRACT

The present invention relates to a novel *Toxoplasma gondii* GRA8-derived recombinant peptide, and a pharmaceutical composition and functional food for preventing or treating cancer, which includes the same as an active ingredient. The *Toxoplasma gondii* GRA8-derived recombinant peptide according to the present invention is a novel recombinant peptide in which a specific mitochondrial targeting sequence and an ATP5A1/SIRT3 sequence of GRA8 are conjugated to an acidity-triggered rational membrane (ATRAM), and has considerably improved efficacy in which an inhibitory concentration 50 (IC50) is improved up to 200-fold (in vitro) or 500-fold (in vivo), compared with a conventional GRA8-derived peptide (rGRA8). In addition, since the peptide treatment shows a notably distinct therapeutic effect in mouse models with cancer, the peptide may be effectively used in a pharmaceutical composition or functional food for preventing or treating cancer.

7 Claims, 9 Drawing Sheets

Specification includes a Sequence Listing.

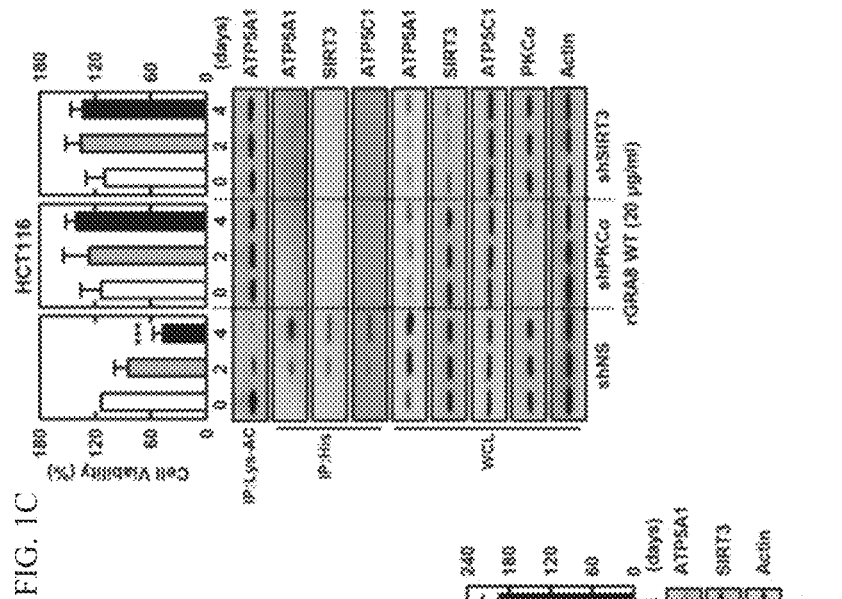
FIG. 1A
FIG. 1B
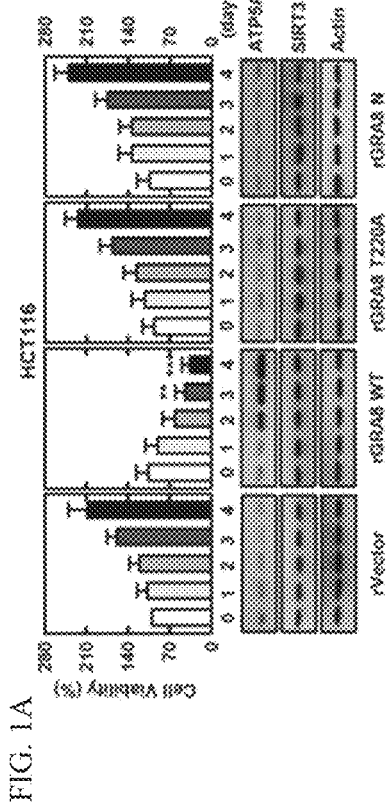
FIG. 1C

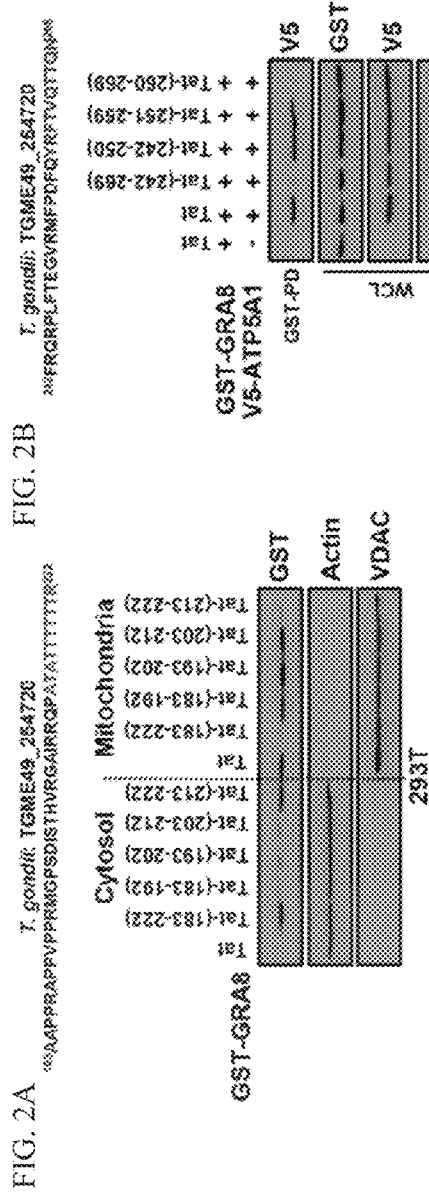
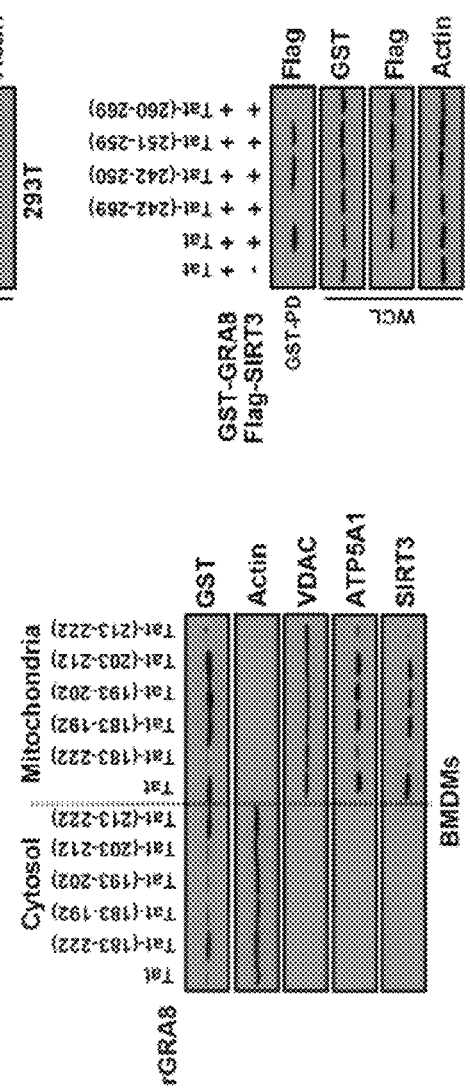
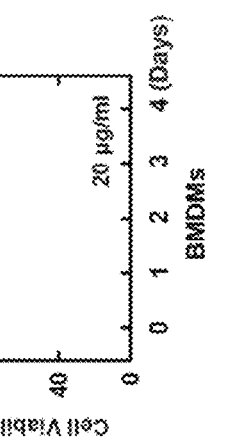
FIG. 2A, FIG. 2B, FIG. 2C, FIG. 2D, FIG. 2E

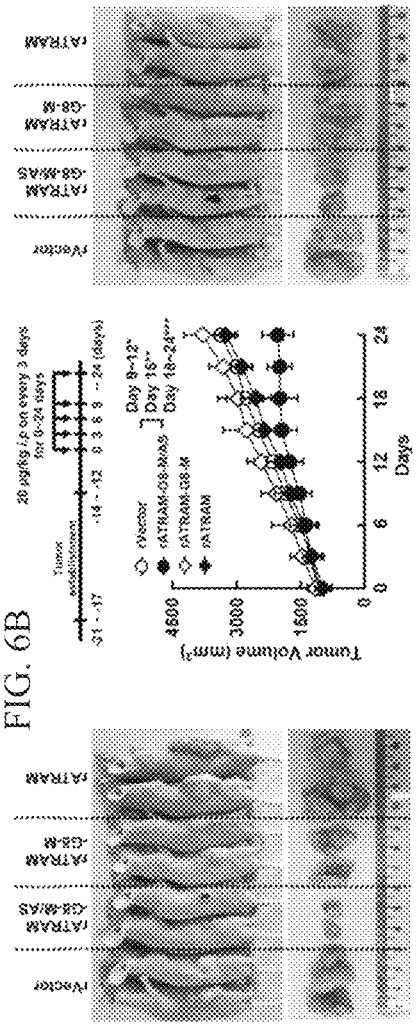
FIG. 6A
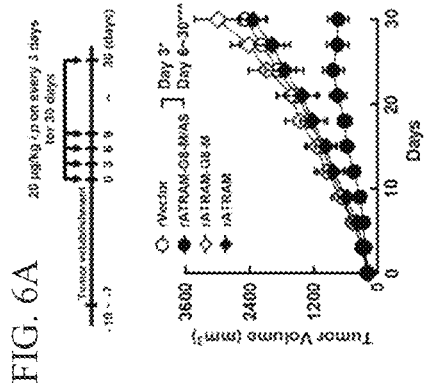
FIG. 6B
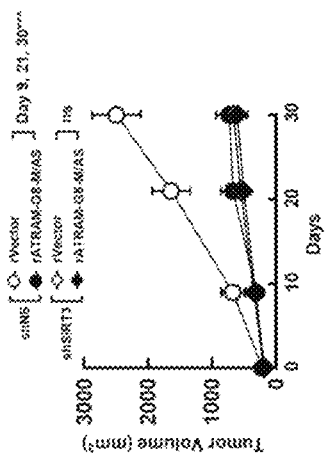
FIG. 6C
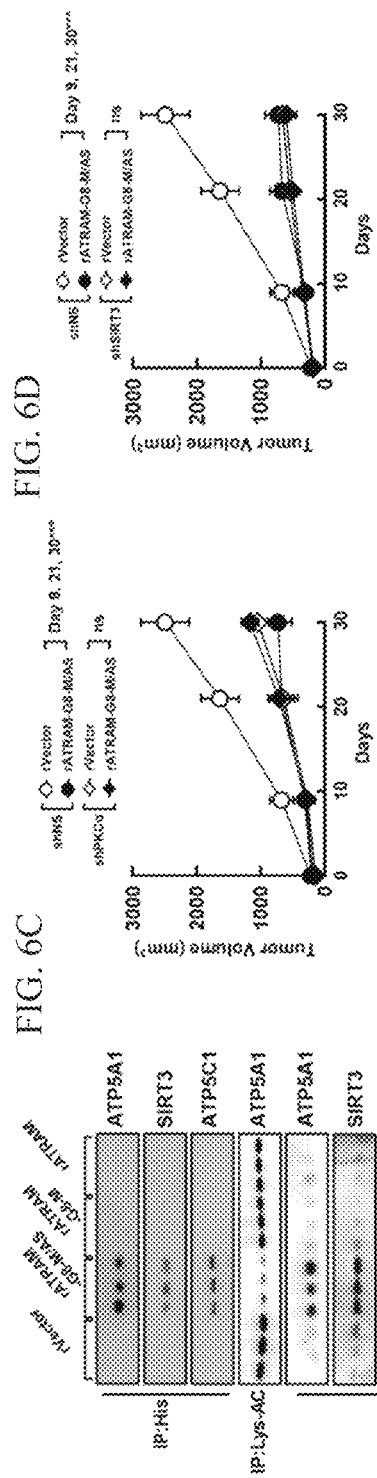
FIG. 6D
FIG. 6E
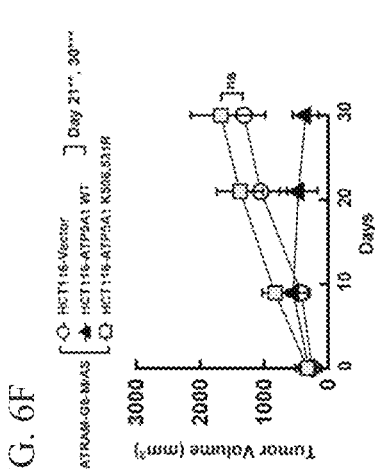
FIG. 6F
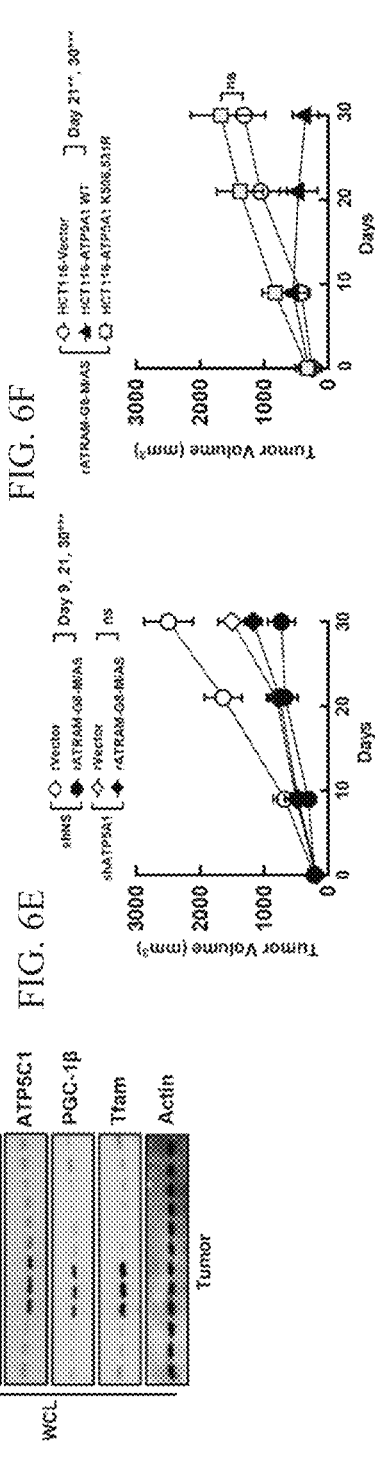

TOXOPLASMA GONDII GRA8-DERIVED RECOMBINANT PEPTIDES AND COMPOSITION FOR PREVENTING OR TREATING CANCER COMPRISING THE SAME

RELATED APPLICATIONS

This application claims the benefit of priority of Korean Patent Application No. KR 10-2019-0174088, filed Dec. 24, 2019, and Korean Patent Application No. KR 10-2020-0100721, filed Aug. 11, 2020, the contents of which are incorporated herein by reference in their entirety.

SEQUENCE LISTING STATEMENT

The ASCII file, entitled 85462SequenceListing.txt, created on Dec. 22, 2020, comprising 7,445 bytes, submitted concurrently with the filing of this application is incorporated herein by reference.

FIELD AND BACKGROUND OF THE INVENTION

The present invention relates to a novel *Toxoplasma gondii* GRA8-derived recombinant peptide, and a composition and functional food for preventing or treating cancer, which include the same.

Cancer is the major cause of death globally, and the second leading cause of death following heart disease in the United States. Metabolism is important in development and prevention of cancer. Cancer cells are metabolically activated and need ATP for growth, proliferation and survival using mitochondrial SIRT3. Therefore, understanding how the metabolic regulators are specifically changed in cancer helps in the development of effective anti-cancer therapies. Mitochondria-targeting therapeutic treatment is considered as a promising strategy for preventing, alleviating or reversing tumor mortality. This regulation known as "metabolic resuscitation" may improve mitochondrial activity pharmacologically or by using a nutritional agent. However, *Toxoplasma gondii* GRA8-mediated mitochondrial and metabolic changes in tumors remain unexplained.

The inventors previously found that protein kinase Cα (PKCα)-phosphorylated *Toxoplasma gondii* GRA8 is transferred to the mitochondria and interacts with mitochondrial SIRT3 [Patent Document 1]. SIRT3 is deacetylated with ATP5A1 and regulates its activity to contribute to antiseptic activity in vivo. The deacetylated ATP5A1 is involved in various mitochondrial processes, and SIRT3 may mediate overall changes in mitochondrial activity, which is critical for tumor growth. SIRT3 may serve as a tumor gene or suppressor, and affect cell death by targeting main regulators and their pathways. Thus, the GRA8-mediated cellular mechanisms that regulate mitochondrial metabolism may be used in therapeutic approaches against tumors similar to strategies used against sepsis.

Meanwhile, peptides and proteins have great potential as therapeutics. Now, small-molecule drugs account for most of the pharmaceutical market; compared with common small-molecule drugs, and peptides and proteins are very selective because they have several contact points with their targets. In addition, enhanced selectivity may reduce side effects and toxicity. Peptides may be designed for a wide range of molecules, and they offer almost infinite possibilities for applications in the fields of oncology, immunology, infectious diseases and endocrinology.

PRIOR ART DOCUMENT

Patent Document (Patent Document 1) Korean Unexamined Patent Application No. 2019-0059389

Non-Patent Document (Non-Patent Document 1) Kim Y R, Kim J S, Yun J S, Kim S, Kim S Y, Jang K, Yang C S. *Toxoplasma gondii* GRA8 induces ATP5A1-SIRT3-mediated mitochondrial metabolic resuscitation: a potential therapy for sepsis. Exp Mol Med. 2018; 50: e464.

Therefore, the inventors had studied to develop significant cell-penetrating peptides in therapeutic approaches, based on the minimum peptide part for mitochondrial targeting and ATP5A1/SIRT3 binding, resulting in designing a novel *Toxoplasma gondii* GRA8-derived recombinant peptide (ATRAM-conjugated multifunctional GRA8 peptide, rATRAM-G8-M/AS) targeting tumor cells in vitro and in vivo, and confirming that the recombinant peptide induces cell death of cancer cells by mitochondrial activation, and anticancer activity is excellent. Thus, the present invention was completed.

SUMMARY OF THE INVENTION

Therefore, the present invention is directed to providing a novel *Toxoplasma gondii* GRA8-derived recombinant peptide Also, the present invention is directed to providing a pharmaceutical composition for preventing or treating cancer, which includes a novel *Toxoplasma gondii* GRA8-derived recombinant peptide as an active ingredient.

Also, the present invention is directed to providing a functional food for preventing or improving cancer, which includes a novel *Toxoplasma gondii* GRA8-derived recombinant peptide.

Also, the present invention is directed to providing a method of preventing or treating cancer, comprising administering a therapeutically effective amount of a *Toxoplasma gondii* GRA8-derived recombinant peptide represented by SEQ ID NO: 1 to a subject.

BRIEF DESCRIPTION OF THE SEVERAL VIEWS OF THE DRAWINGS

The above and other objects, features and advantages of the present invention will become more apparent to those of ordinary skill in the art by describing in detail exemplary embodiments thereof with reference to the attached drawings, in which:

FIGS. 1A, 1B and 1C: confirms that rGRA8 treatment increases HCT116 cell death by mitochondria pathways [(A and B). Various cancer cells were incubated with WT rGRA8 (20 μg/ml) and its mutants for indicated times and then cell viability was measured by MTT analysis (upper) and αATP5A1, αSIRT3 or αActin immunoblotting (lower) was performed. (C) HCT116 cells were transduced with lentivirus-shRNA-NS or lentivirus-shRNA-PKCα or SIRT3 (MOI=100) with polybrene (8 μg/mL) (right) for 2 days. The cells were incubated with WT rGRA8 for indicated times and subjected to IP with αLys-AC or αHis and IB with αATP5A1, αATP5C1, αSIRT3, αPGC-1, αPKCα or αActin. Data represents five independent experiments with similar results. Significant differences were determined by comparison with rVector treatment ( P<0.01; * P<0.001)].

FIGS. 2A, 2B, 2C, 2D and 2E show the design and expression of an ATRAM-conjugated multifunctional GRA8 peptide (rATRAM-G8-M/AS)-based protein [(A) Subcellular fractionation of 293T cells was performed by expression of GST-GRA8 WT or incubation of WT rGRA8 with (1 μg/ml) BMDM and treatment with several Tat-GRA8 peptides for 6 hours (10 μM). Mitochondrial and cytosolic fractions were fractionated and analyzed for expression of GST by IB. The purity of the fractions was confirmed by blotting for VDAC (mitochondrial protein) and actin (cytosolic protein). (B) A mammalian GST-GRA8 construct was transfected into 293T cells for 12 hours with V5-ATP5A1 or Flag-SIRT3, and treated with several Tat-GRA8 peptides (10 μM) for 6 hours. The 293T cells were used for GST pulldown, followed by IB with αV5 or αFlag. WCL was used for IB with αGST, αV5, αFlag or αActin. (C) The schematic design of ATRAM-GRA8-M/AS and its mutants [ATRAM-G8-M/AS (SEQ ID NO: 1), ATRAM-G8-M (SEQ ID NO: 2), ATRAM (SEQ ID NO: 3)]. (D) 6×His-rATRAM-GRA8-M/AS purified with bacteria and its mutants were analyzed by Coomassie blue staining (left) or αHis immunoblotting (IB; right). (E) BMDM was incubated with rATRAM-GRA8-M/AS and its mutant (20 μg/ml) for indicated times, and cell viability was then measured by an MMT assay. Data represents four independent experiments with similar results (A, B, D and E)].

FIGS. 6A, 6B, 6C, 6D, 6E and 6F show the antitumor activity of rATRAM-GRA8-M/AS in HCT116 xenografts [(A and B) the schematic diagram of a xenograft model treated with rATRAM-GRA8-M/AS or its mutants (upper). HCT116 cells were subcutaneously injected into the flank of a nude mouse. The length and width of a tumor were measured using calipers every third day for 30 days. On day 15 after administration, the mice were euthanized, and the interaction with GRA8, acetylation levels of ATP5A1 or expression of OXPHOS was analyzed (A, lower). The representative images of tumors from mice treated with rATRAM-GRA8-M/AS or mutants on day 15 (right). (C-F) HCT116 cells were transduced with lentivirus-shRNA-NS or lentivirus-shRNA-PKCα, SIRT3, or polybrene (C-E) or ATP5A1 WT or mutant-expressing HCT116 cells were subcutaneously injected into the flank of a nude mouse. Significant differences (* P<0.05;  P<0.01; * P<0.001) were determined by comparison with rVector. Each group included 10 mice. Data represents two independent experiments with similar results]

DESCRIPTION OF SPECIFIC EMBODIMENTS OF THE INVENTION

Figure 3:
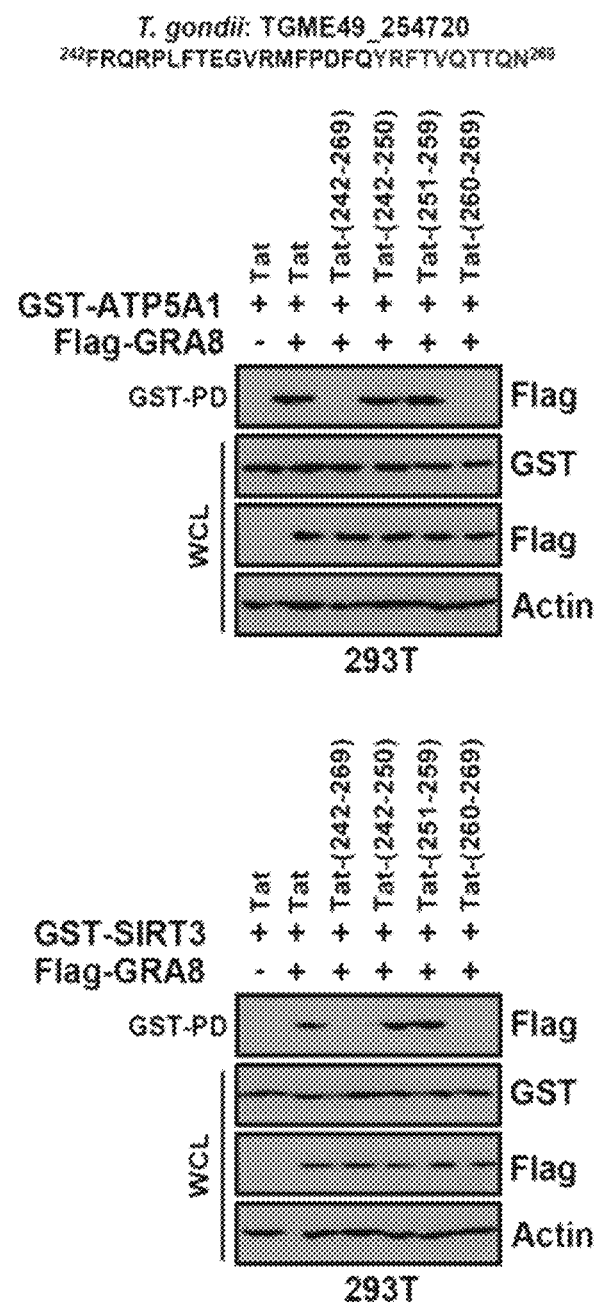
FIG. 3 shows that the minimal region of the confirmed GRA8 directly interacts with ATP5A1 and SIRT3 [Mammalian GST-ATP5A1 or GST-SIRT3 was constructed with Flag-GRA8, and 12 hours after transfection, 293T was treated with several Tat-GRA8 peptides (10 μM) for 6 hours. 293T cells were used for GST pulldown, followed by performing IB with anti-Flag. A whole cell lysate is used for IB with αGST, αFlag or anti-actin. Data represents four independent experiments with similar results].

Hereinafter, exemplary embodiments of the present invention will be described in detail. However, the present invention is not limited to the embodiments disclosed below and can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

The terminology used herein is for the purpose of describing particular embodiments only and is not intended to be limiting the exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof and do not preclude the presence or addition of one or more other features, integers, steps, operations, elements, components and/or groups thereof.

With reference to the appended drawings, exemplary embodiments of the present invention will be described in detail below. To aid in understanding of the present invention, like numbers refer to like elements throughout the description of the figures, and the description of the same elements will not be iterated.

One aspect of the present invention provides a *Toxoplasma gondii* GRA8-derived recombinant peptide.

The "*Toxoplasma gondii* GRA8-derived recombinant peptide" used herein refers to an ATRAM-conjugated multifunctional GRA8 peptide having an amino acid sequence of (GLAGLAGLLGLLEGLLGLPLGLLEGLWL-GLELEGN)$_2$-GG-ATATTTTTR-GG-YRFTVQTTQN, represented by SEQ ID NO: 1 and named rATRAM-G8-M/AS herein. In addition, a mutant of the peptide is included in the scope of the present invention. A mutant of the peptide refers to a protein having a different sequence from the amino acid sequence of a recombinant peptide by deletion, insertion, non-conservative or conservative substitution of one or more amino acid residues or a combination thereof. Amino acid exchanges in proteins and fragments that do not entirely alter the activity of a molecule are known in the art (H. Neurath, R. L. Hill, The Proteins, Academic Press, New York, 1979).

The term "dense granule antigen 8 (GRA8; GenBank Accession No. XP-002369526.1)" refers to a *Toxoplasma gondii*-derived antigen protein, and consists of a 269-amino acid sequence of SEQ ID NO: 2. GRA8 is an acute phase-specific antigen that enables parasite survival in host cells, and has been reported as a promising vaccine candidate against toxoplasmosis (J. G. Costa et. al., Microb. Pathog., 100:229-236, 2016).

Figure 9:
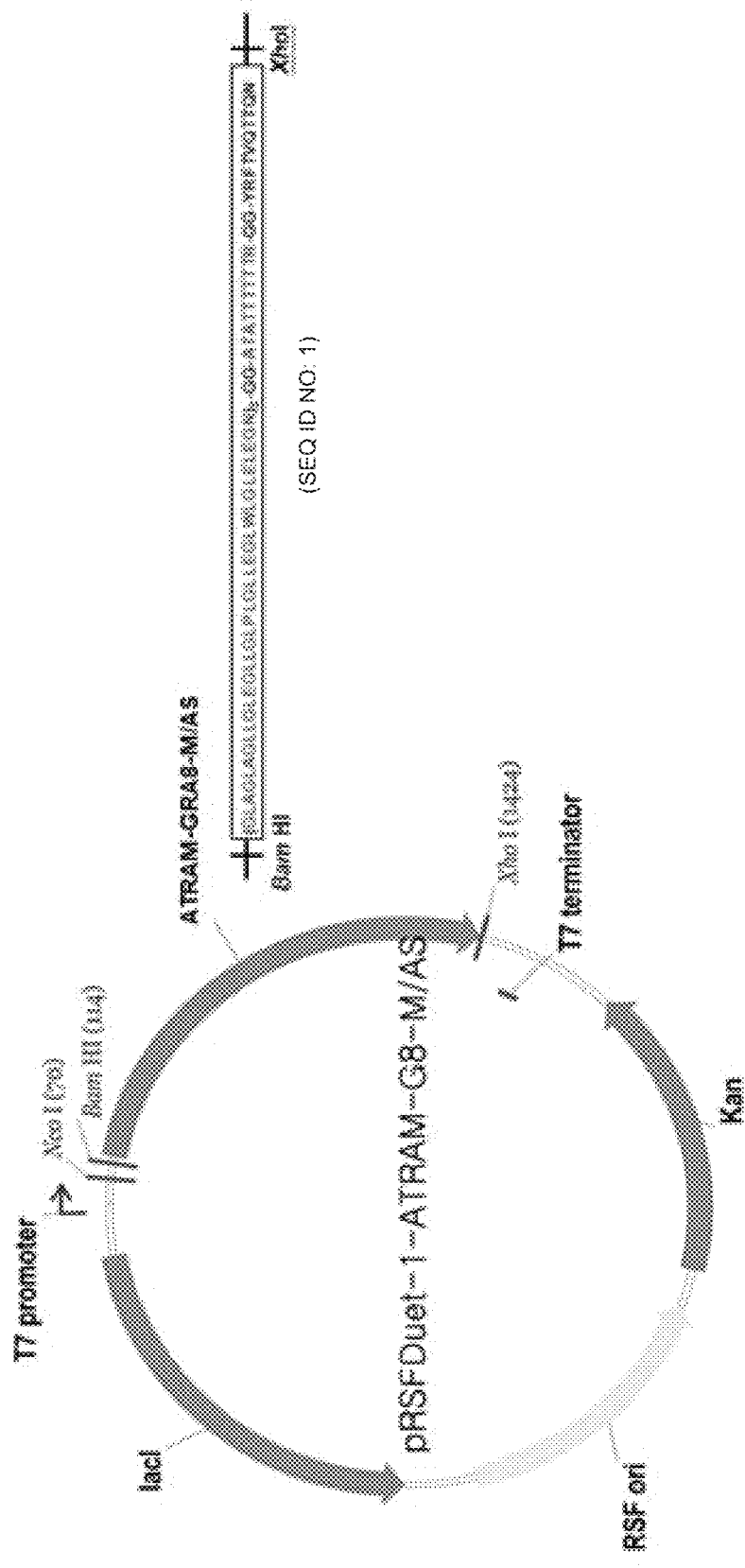
FIG. 9 shows the cleavage map of a recombinant expression vector pRSFDuet-1-ATRAM-G8-M/AS according to the present invention [ATRAM-GRA8-M/AS (SEQ ID NO: 1)].

FIG. 9 shows the cleavage map of a recombinant expression vector pRSFDuet-1-ATRAM-G8-M/AS according to the present invention.

Another aspect of the present invention provides a polynucleotide (gene) encoding the *Toxoplasma gondii* GRA8-derived recombinant peptide.

The polynucleotide includes a base sequence of SEQ ID NO: 5 (ggcctggccg gcctggccgg cctgctgggc ctggaaggcc tgccgggcct gccctgggc ctgctggaag gcctgtggct gggcctggaa ctggaaggaa acggcctggc cggcctggcc ggcctgctgg gcctggaagg cctgccgggc ctgccctgg gcctgctgga aggcctgtgg ctgggcctgg aactggaagg aaacggggg gctaccgcca ccacaaccac tacccgcgggggagat tcaccgtcca aacgacgcag aattaa).

In addition, a homolog of the base sequence is included in the scope of the present invention. Specifically, the polynucleotide may include a base sequence having 70% or more, more preferably, 80% or more, even more preferably 90% or more, and most preferably 95% or more homology with a base sequence selected from the group consisting of the base sequences of SEQ ID NO: 1. The "% homology" for a polynucleotide is confirmed by comparing two optimally aligned sequences and a comparative region, and a part of a polynucleotide sequence in the comparative region may include additions or deletions (that is, a gap), rather than a reference sequence (not including additions or deletions) for the optimal alignment of two sequences.

The "codon optimization" refers to an alteration in a codon of a polynucleotide encoding a protein, which is primarily used in a specific organism to more effectively express an encoded protein in an organism. Although the genetic code is degenerate since most amino acids are represented by some codons called "synonyms" or "synonymous" codons, codon usage by a specific organism is not arbitrary but biased towards certain codon triplets. Such codon usage bias may be higher with respect to a predetermined gene, a gene with a common function or ancestral origin, a highly expressed protein versus a low copy number protein, and a collective protein coding region of the genome of an organism. In the present invention, the base sequence of SEQ ID NO: 3 is a sequence optimized for an *E. coli* codon to express a gene in *E. coli*.

Still another aspect of the present invention provides a recombinant expression vector which includes *Toxoplasma gondii* GRA8-derived recombinant peptide.

Yet another aspect of the present invention provides a recombinant vector including the SV82 polypeptide-coding gene, and *E. coli* transformed with the recombinant vector.

The term "recombinant" cell refers to a cell replicating a heterologous nucleic acid, expressing the nucleic acid, or expressing proteins encoded by a peptide, a heterologous peptide or a heterologous nucleic acid. Recombinant cells may express a gene or gene fragment not found in a natural form of the cells in one of sense and antisense forms. In addition, recombinant cells may express a gene found in natural-state cells, but the gene is modified, and reintroduced into cells by an artificial means.

In the present invention, the *Toxoplasma gondii* GRA8-derived recombinant peptide-coding gene may be inserted into a recombinant expression vector. The term "recombinant expression vector" refers to a bacterial plasmid, a phage, an enzyme plasmid, a plant cell virus, a mammalian cell virus, or other vectors. Generally, any plasmid and vector may be used as long as they can be replicated and stabilized in a host. A major characteristic of the expression vector is that it has a replication origin, a promoter, a marker gene and a translation control element.

An expression vector including a gene sequence encoding a *Toxoplasma gondii* GRA8-derived recombinant peptide and suitable transcription/translation control signals may be constructed by a method well known by those of ordinary skill in the art. The method includes in vitro recombinant DNA technology, DNA synthesis technology and in vivo recombination technology. The DNA sequence may be effectively linked to a suitable promoter in the expression vector to trigger mRNA synthesis. In addition, the expression vector may include a ribosome-binding site and a transcription terminator as a translation initiation site.

The recombinant vector according to an embodiment of the present invention was manufactured by in-frame fusion of a gene encoding a *Toxoplasma gondii* GRA8-derived recombinant peptide synthesized in a pRSFDuet-1 vector (SEQ ID NO: 2) to the 5' end (BamHI restriction enzyme site) and the 3' end (XhoI restriction enzyme site), and is a vector that effectively expresses the gene by a T7 promoter and a lac operator to manufacture a *Toxoplasma gondii* GRA8-derived recombinant peptide.

Host cells that can stably and continuously clone and express the vector of the present invention in prokaryotic cells may be any host cells known in the art, and are Enterobacteriaceae and strains such as *E. coli* Rosetta, *E. coli* JM109, *E. coli* BL21, *E. coli* RR1, *E. coli* LE392, *E. coli* B, *E. coli* X 1776, *E. coli* W3110, *Bacillus* strains such as *Bacillus subtilis, Bacillus thuringiensis, Salmonella typhimurium, Serratia marsessons*, and various *Pseudomonas* sp.

In addition, when the vector of the present invention is transformed into eukaryotic cells, as host cells, yeast (*Saccharomyces cerevisiae*), insect cells, human cells (e.g., Chinese hamster ovary (CHO) cell line), W138, BHK, COS-7, 293, HepG2, 3T3, RIN and MDCK cell line) and plant cells, may be used.

The host cells transformed with the recombinant vector according to an embodiment of the present invention may be *E. coli*, but the present invention is not limited thereto.

A method of delivering the vector of the present invention into host cells may be performed by a $CaCl_2$ method, a Hanahan method (Hanahan, D., 1983 J. Mol. Biol. 166, 557-580) and an electroporation method when host cells are prokaryotic cells. In addition, when the host cells are eukaryotic cells, a vector may be injected into host cells through microinjection, calcium phosphate precipitation, electroporation, liposome-mediated transfection, DEAE-dextran treatment, and gene bombardment.

In one embodiment of the present invention, a target peptide (G8-M/AS) binding to mitochondrial SIRT3 protein in the base sequence of *Toxoplasma gondii* GRA8 was obtained. An expression vector was obtained by inserting a base sequence binding to a cancer cell target ATRAM peptide, a transformant producing rATRAM-G8-M/AS was obtained by introducing the expression vector into *E. coli*, and the transformant was cultured to mass-produce and purify recombinant rATRAM-G8-M/AS. In addition, as a result of immunoblotting (IB) assay for the purified recombinant rATRAM-G8-M/AS, it was confirmed that the rATRAM-G8-M/AS has excellent cancer cell targetability (FIG. 5), and mitochondrial activity (Oxphos V activity, mitochondrial mass and ATP production) in cancer cells are induced (FIG. 4). Therefore, since the rATRAM-G8-M/AS affects mitochondrial biosynthesis and activity, it was able to inferred that it can be used in treatment of cancer caused by mitochondrial dysfunction.

In addition, in terms of cell death of a cancer cell line by the rATRAM-G8-M/AS-induced mitochondrial activation according to the present invention, it was confirmed that the rATRAM-G8-M/AS has an effect of an approximately 200-fold improved inhibitory concentration 50, compared with a conventional GRA8-derived peptide (rGRA8) (FIG. 4). In addition, in terms of the anti-tumor activity in a cancer cell line, the rATRAM-G8-M/AS showed an effect of an approximately 500-fold improved inhibitory concentration 50, compared with the conventional GRA8-derived peptide (rGRA8).

Yet another aspect of the present invention provides a pharmaceutical composition for preventing or treating cancer, which includes a novel *Toxoplasma gondii* GRA8-derived recombinant peptide as an active ingredient.

The cancer may be selected from the group consisting of brain cancer, esophageal cancer, stomach cancer, liver cancer, pancreatic cancer, kidney cancer, small intestine cancer, colon cancer, rectal cancer, lung cancer, breast cancer, uterine cancer, ovarian cancer and prostate cancer.

The term "colorectal cancer" used herein refers to a malignant tumor consisting of cancer cells generated in the large intestine. Specifically, the colorectal cancer is a combination of cancers generated in the colon and the rectum.

The term "prevention" used herein refers to all actions of inhibiting colorectal cancer or delaying the onset thereof by administration of the pharmaceutical composition of the present invention, and the "treatment" refers to all actions involved in alleviating or beneficially changing symptoms of already occurring colorectal cancer by administration of the pharmaceutical composition of the present invention.

Particularly, it can be seen that the rATRAM-G8-M/AS provided in the present invention may be used as an active ingredient of a pharmaceutical composition having an effect of preventing or treating cancer, particularly, colorectal cancer.

The pharmaceutical composition of the present invention may further include a pharmaceutically acceptable carrier. The term "pharmaceutically acceptable" means exhibiting a characteristic of being non-toxic to cells or a human exposed to the composition.

The carrier may be any one known in the art, such as a buffer, a preservative, a painkiller, a solubilizer, an isotonic agent, a stabilizer, a base, an excipient, or a lubricant, without limitation.

In addition, the pharmaceutical composition of the present invention may be used by being formulated in oral formulations such as a powder, a granule, a tablet, a capsule, a suspension, an emulsion, a syrup and an aerosol, a preparation for external use, a suppository and a sterile injectable solution according to conventional methods. As a carrier, an excipient and a diluent that can be included in the composition of the present invention, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate and mineral oil may be used. In preparation, generally used diluting agents or excipients such as a filler, a thickening agent, a binder, a wetting agent, a disintegrating agent and a surfactant are used.

The pharmaceutical composition may be administered through any common route that can reach target tissue.

The "administration" used herein refers to introduction of a certain material to a patient by any suitable method, and here, the material is formulated for human or veterinary use and administered by various routes. The recombinant peptide of the present invention may be administered via a parenteral route, for example, intravascularly, intravenously, intraarterially, intramuscularly or subcutaneously, orally, intranasally, intrarectally, transdermally or an inhalation route using an aerosol, or administered by bolus or infusion, and preferably intramuscularly or subcutaneously injected.

Meanwhile, the pharmaceutical composition of the present invention is administered at a pharmaceutically effective amount. The "pharmaceutically effective amount" used herein refers to an amount sufficient for treating a disease at a reasonable benefit/risk ratio applicable for medical treatment, and an effective dosage may be determined by parameters including a health condition of a patient, severity, drug activity, sensitivity to a drug, an administration method, administration time, an administration route and an excretion rate, the duration of treatment and drugs combined or simultaneously used, and other parameters well known in the medical field.

The pharmaceutical composition of the present invention may be administered separately or in combination with other therapeutic agents, and may be sequentially or simultaneously administered with a conventional therapeutic agent, or administered in a single or multiple dose(s). In consideration of all of the above-mentioned parameters, it is important to achieve the maximum effect with the minimum dose without a side effect, and such a dose may be easily determined by one of ordinary skill in the art.

The other conventional anticancer agents may be, but is not limited thereto, any one or more selected from the group consisting of cetuximab, erlotinib, gefitinib, trastuzumab, lapatinib, paclitaxel, tamoxifen, and cisplatin.

The pharmaceutical composition of the present invention may include one or more of known active ingredients having an effect of preventing and treating cancer along with the rATRAM-G8-M/AS.

Yet another aspect of the present invention provides a method of preventing or treating cancer, which includes administering the pharmaceutical composition to a subject who is expected to have cancer or already has cancer.

Also, A method of preventing or treating cancer, comprising administering a therapeutically effective amount of a *Toxoplasma gondii* GRA8-derived recombinant peptide represented by SEQ ID NO: 1 to a subject.

The term "subject" used herein refers to a living organism that has or may develop cancer, and includes all mammals, for example, primates including a human, cows, horses, sheep, pigs, chickens, turkeys, quails, cats, dogs, mice, rats, rabbits or guinea pigs. The pharmaceutical composition of the present invention may be administered to a subject to effectively prevent or treat the cancer. The pharmaceutical composition of the present invention may be administered in combination with a conventional therapeutic.

Specifically, an effective amount of the rATRAM-G8-M/AS contained in the composition according to the present invention may vary according to a patient's age, sex and body weight, and generally, the rATRAM-G8-M/AS of the present invention may be administered, based on solids, at 0.001 to 50 mg per kg of body weight, and preferably, 0.1 to 15 mg per kg of body weight daily or every other day, or one to three doses a day. However, the effective amount may be increased or decreased depending on the route of administration, the severity of obesity, sex, a body weight or age, and thus it does not limit the scope of the present invention in any way.

Yet another aspect of the present invention provides a functional food for preventing or improving cancer, which includes the rATRAM-G8-M/AS.

The term "improvement" used herein refers to all types of actions that at least reduce parameters related to a condition to be treated, for example, the severity of a symptom.

When the composition of the present invention is used as food, the "rATRAM-G8-M/AS" may be added as it is or used along with a different food or food ingredient, and may be suitably used according to a conventional method. The composition may include a sitologically acceptable food supplement in addition to active ingredients, and a mixing amount of the active ingredients may be suitably determined by the purpose of use (prevention, health or therapeutic treatment).

The term "food supplement" used herein refers to an ingredient that can be added auxiliarly to a food, and is added to produce each form of functional food and may be suitably selected and used by those of ordinary skill in the art. Examples of food supplements include various nutritional supplements, vitamins, minerals (electrolytes), flavoring agents such as synthetic flavoring agents and natural flavoring agents, coloring agents and fillers, pectic acid and a salt thereof, alginic acid and a salt thereof, organic acids, protective colloidal thickening agents, pH adjustors, stabilizers, preservatives, glycerin, alcohols, carbonating agents used in carbonated soft drinks, but the type of food supplement of the present invention is not limited thereto.

The term "functional food" used herein refers to a food manufactured and processed in the form of a tablet, a capsule, a powder, a granule, a liquid and a pill using a raw material or ingredient having useful functionality for the human body. Here, the "functionality" refers to regulation of nutrients for the structure and function of the human body or having a useful effect for health purposes such as a physiological action. The functional food of the present invention may be produced by a method conventionally used in the art, and produced by adding raw materials and ingredients conventionally added in the art in production. In addition, the functional food may be produced in any formulation recognized as a functional food without limitation. The food composition of the present invention may be prepared in various types of formulations, and unlike general drugs, it has an advantage of having no side effects that may occur when a drug is taken for a long time by using food as a raw material and excellent portability, and thus the functional food of the present invention can be taken as a supplement for improving an effect of rheumatoid arthritis.

A *Toxoplasma gondii* GRA8-derived recombinant peptide according to the present invention is a novel recombinant peptide in which a specific mitochondrial targeting sequence of GRA8 and an ATP5A1/SIRT3 sequence are conjugated to an acidity-triggered rational membrane (ATRAM), and exhibits an excellent effect of preventing or treating cancer, particularly, colorectal cancer, and thus can be effectively used as a pharmaceutical composition or functional food for preventing or treating cancer.

Hereinafter, the present invention will be described in detail with reference to examples thereof. However, it should be understood that the following examples are just preferred examples for the purpose of illustration only and is not intended to limit or define the scope of the invention. The following examples described herein are provided in order to make the present invention more comprehensive and complete and provide the scope of the present invention to those skilled in the art to which the present invention belongs and thus will be defined by the appended claims equivalents thereof.

EXAMPLES

[Materials and Methods]

All animal experimental procedures were reviewed and approved by the Institutional Animal Care and Use Committee (protocol 2016-0221 and 2017-0218) and the Institutional Review Board (HYI-17-227-1) of Hanyang University. All animal experiments were performed according to Korean Food and Drug Administration guidelines.

Mice and Cell Culture

Wild-type C57BL/6 and BALB/c mice were purchased from Orient Bio (Gyeonggi-do). Bone marrow-derived macrophages (BMDMs) were isolated from C57BL/6 mice and cultured in DMEM containing M-CSF (R & D Systems, 416-ML) for 3 to 5 days (see Toxoplasma gondii GRA7-Targeted ASC and PLD1 Promote Antibacterial Host Defense via PKCalpha. PLoS Pathog. 2017; 13:e1006126). HEK293T cells (ATCC-11268; American Type Culture Collection), HCT116 (ATCC-CCL247), HT-29 (ATCC-HTB-38), HepG2 (ATCC-HB-8065), Hep3B (ATCC-HB-8064), MCF7 (ATCC-HTB-22) and MDAMB-231 (ATCC-HTB-26) were maintained in DMEM (Invitrogen) containing 10% FBS (Invitrogen), sodium pyruvate, a non-essential amino acid, penicillin G (100 IU/ml) and streptomycin (100 μg/ml), and transient transfection was performed using Lipofectamine 3000 (Invitrogen) or calcium phosphate (Clontech) according to the manufacturer's instructions. Stable HCT116 cell lines were generated using a standard selection protocol with 400-800 μg/ml of G418.

Recombinant ATRAM-GRA8 Mito-ATP5A1/SIRT3 Protein

Figure 8:
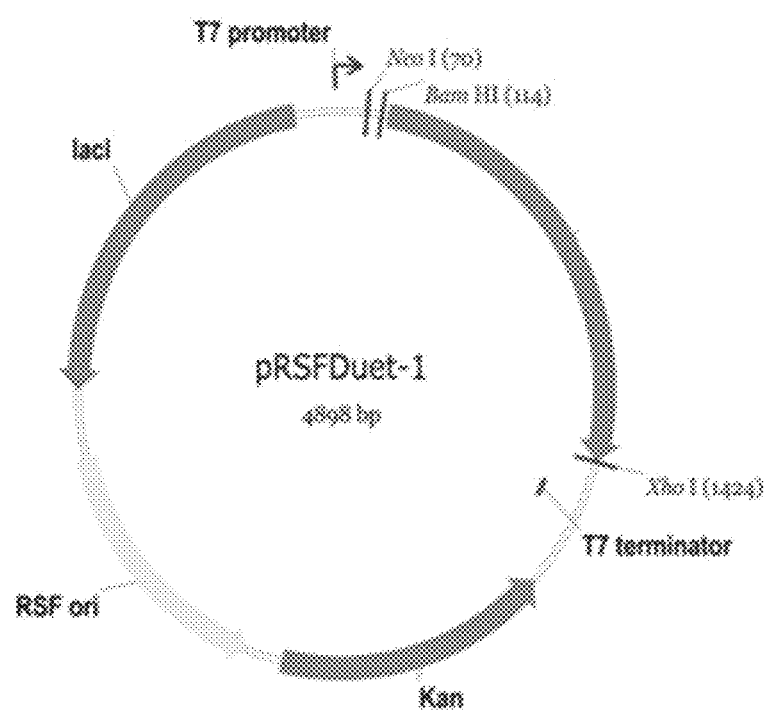
FIG. 8 shows the cleavage map of a pRSFDuet-1 vector used in manufacture of a recombinant vector according to the present invention.

To obtain ATRAM amino acid residues (GLAGLAGLLGLEGLLGLPLGLLEGLWLGLELEGN: SEQ ID NO: 6), a mitochondrial targeting sequence (ATATTTTTR: SEQ ID NO: 7) and an ATP5A1/SIRT3 binding sequence (YRFTVQTTQN: SEQ ID NO: 8), a recombinant purified protein was used by insertion and cloning in an N-terminal 6xHis tagged pRSFDuet-1 vector (Novagen; FIG. 8) according to the standard protocols of Novagen. Here, E. coli BL-21 (DE-3) pLysS was used as a protein expression host according to the standard protocol recommended by Novagen, which is the vector manufacturer, and protein expression was induced in the E. coli strain, and the resulting protein was harvested and purified. rGRA8 was dialyzed with a permeable cellulose membrane and tested for lipopolysaccharide contamination with a Limulus amebocyte lysate assay (BioWhittaker), and the concentration of the rGRA8 protein used in the experiment described herein was <20 μg/ml.

Reagents and Antibodies

Human PKCα (RHS4531-EG5578) and SIRT3 (RHS4531-EG23410)-targeting shRNA plasmid DNA was purchased from Open Biosystems. Specific antibodies against ATP5C1 (PA5-29975) were purchased from Invitrogen. Antibodies specific for ATP5A1 (51), SIRT3 (14.45), VDAC (B-6), SDHA (B-1), UQCRC2 (G-10), COX IV (D-20), PGC-1β (E-9), Tfam (H-203), PKCα (C-20), Actin (1-19), V5 (H-9), Flag (D-8), His (AD1.1.10), Lys-AC (AKL5C1) and GST (B-14) were purchased from Santa Cruz Biotechnology.

Plasmid Construction

Plasmids encoding the full-length of GRA8 (GST or Flag-GRA8), ATP5A1 (GST or V5-ATP5A1) and SIRT3 (GST or Flag-SIRT3) plasmids were described in Non-Patent Document 1. The plasmids used herein are listed in Table 1 below.

TABLE 1

| Name | Expression | Tag or Clon ID | References |
|---|---|---|---|
| pET23b-Vector | Bacterial expression | His | Non-Patent Document 1 |
| pET23b-GRA8 WT (1-269) | Bacterial expression | His | Non-Patent Document 1 |
| pET23b-GRA8 T220A | Bacterial expression | His | Non-Patent Document 1 |
| pET23b-GRA8 N (1-241) | Bacterial expression | His | Non-Patent Document 1 |
| pEBG-GRA8 WT (1-269) | Mammalian expression | GST | Non-Patent Document 1 |
| pcDNA3-ATP5A1 | Mammalian expression | V5 | Non-Patent Document 1 |
| pcDNA3-ATP5A1 (K506, 531R) | Mammalian expression | V5 | Non-Patent Document 1 |
| pcDNA3-SIRT3 | Mammalian expression | Flag | Non-Patent Document 1 |
| pRSFDuet-1-ATRAM-G8-M/AS | Bacterial expression | His | FIG. 9 |
| pRSFDuet-1-ATRAM-G8-M | Bacterial expression | His | |
| pRSFDuet-1-ATRAM | Bacterial expression | His | |
| pGIPZ-shPKCα | Human | V2LHS_218226, V2LHS_87125, V2LHS_170435, V2LHS_170433 Purchased from Horizon Discovery Dharmacon | — |
| pGIPZ-shSIRT3 | Human | V3LHS_365648, V3LHS_347987, V3LHS_365650 Purchased from Horizon Discovery Dharmacon | — |
| pGIPZ-shATP5A1 | Human | V2LHS_192755, V2LHS_218429 V3LHS_375667, V3LHS_375664 Purchased from Horizon Discovery Dharmacon | — |

Peptides

A Tat-conjugated GRA8 peptide was commercially synthesized and purified in the form of an acetate salt by Peptron (Korea) to avoid an abnormal reaction in cells. The amino acid sequences of the peptides used herein are described in Tables 2 and 3 below. An endotoxin content measured by a Limulus amebocyte lysate assay (BioWhittaker) was less than 3 to 5 μg/ml at the concentration of the peptide used in the experiment.

TABLE 2

Amino acid sequence of Toxoplasma gondii
(T. gondii) GRA8 (SEQ ID NO: 2)

| Gene | Accession no | Sequence |
|---|---|---|
| TGME49_254720 | XP_002369526.1 | MALPLRVSATVFVVFAVFGVARAMNGPLSYHPSSYGASYPNPSNP<br>LHGMPKPENPVRPPPPGFHPSVIPNPPYPLGTPAGMPQPEVPPLQ<br>HPPPTGSPPAAAPQPPYPVGTPGMPQPEIPPVHRPPPPGFRPEVA<br>PVPPYPVGTPTGMPQPEIPAVHHPFPYVTTTTTAAPRVLVYKIPY<br>GGAAPPRAPPVPPRMGPSDISTHVRGAIRRQPATATTTTTRNVLL<br>RTAILAAAAATLIALFRQRPLFTEGVRMFPDFQYRFTVQTTQN |

TABLE 3

Sequence of T. gondii GRA8 peptide

| Name | Sequence (N → C) |
|---|---|
| Tat | GRKKRRQRRR (SEQ ID NO: 9) |
| Tat-GRA8-<br>(183-222) | GRKKRRQRRR-G-AAPPRAPPVPPRMGPSD<br>ISTHVRGAIRRQPATATTTTTR<br>(SEQ ID NO: 10) |
| Tat-GRA8-<br>(183-192) | GRKKRRQRRR-G-AAPPRAPPVP<br>(SEQ ID NO: 11) |
| Tat-GRA8-<br>(193-202) | GRKKRRQRRR-G-PRMGPSDIST<br>(SEQ ID NO: 12) |
| Tat-GRA8-<br>(203-212) | GRKKRRQRRR-G-HVRGAIRRQP<br>(SEQ ID NO: 13) |
| Tat-GRA8-<br>(213-222) | GRKKRRQRRR-G-ATATTTTTR<br>(SEQ ID NO: 14) |
| Tat-GRA8-<br>(242-269) | GRKKRRQRRR-G-FRQRPLFTEG<br>VRMFPDFQYRFTVQTTQN<br>(SEQ ID NO: 15) |
| Tat-GRA8-<br>(242-250) | GRKKRRQRRR-G-FRQRPLFTE<br>(SEQ ID NO: 16) |
| Tat-GRA8-<br>(251-259) | GRKKRRQRRR-G-GVRMFPDFQ<br>(SEQ ID NO: 17) |
| Tat-GRA8-<br>(260-269) | GRKKRRQRRR-G-YRFTVQTTQN<br>(SEQ ID NO: 18) |

GST Pulldown, Immunoblotting and Immunoprecipitation Assays

GST pulldown, immunoprecipitation and immunoblotting assays were explained in C. S. Yang et al., Nat. Commun., 6:6115 (2015) and H. J. Koh et al., PLoS Pathog., 13(1): e1006126 (2017). For GST pulldown, cells were obtained and lysed in an NP-40 buffer supplemented with a complete protease inhibitor cocktail (Roche). After centrifugation, the supernatant was pre-purified with protein A/G beads at 4° C. for 2 hours. The pre-purified lysate was mixed with a 50% slurry of glutathione-conjugated Sepharose beads (Amersham Biosciences), and the binding reaction was performed at 4° C. for 4 hours. The precipitate was washed with a lysis buffer several times. Proteins bound to glutathione beads were eluted with an SDS loading buffer by heating for 5 minutes.

For immunoprecipitation, cells were obtained, and then lysed in an NP-40 buffer supplemented with a complete protease inhibitor cocktail (Roche). After pre-purification with A/G agarose beads at 4° C. for 1 hour, a whole cell lysate was used for immunoprecipitation with indicated antibodies. Generally, 1 to 4 μg of commercial antibodies were added to 1 ml of the cell lysate, and incubated at 4° C. for 8 to 12 hours. After the addition of the protein A/G agarose beads for 6 hours, the immunoprecipitate was washed with a lysis buffer several times and heated for 5 minutes to be eluted with an SDS loading buffer.

For immunoblotting, polypeptides were subjected to electrophoresis (PAGE) with an SDS-polyacrylamide gel, and then transferred to a PVDF membrane (Bio-Rad) for separation. Immunodetection was performed with a specific antibody. Antibody binding was visualized by chemiluminescence (ECL; Millipore) and detected by a Vilber chemiluminescence analyzer (Fusion SL 3; Vilber Lourmat).

Cellular Fractionation

Cytosol and mitochondria were isolated from cells using a mitochondria fractionation kit (Active Motif, 40015) or as described in Toxoplasma gondii GRA8 induces ATP5A1-SIRT3-mediated mitochondrial metabolic resuscitation: a potential therapy for sepsis. Exp Mol Med. 2018; 50:e464. A subcellular fractionated protein was lysed in a buffer containing 2% SDS and heated with a 2× reducing sample buffer for SDS-PAGE.

MTT Assay

As described in Non-Patent Document 1, the cell viability for a non-treated group was measured by an MTT assay. After incubation for an indicated time, 5 mg/ml of a 3-(4, 5-dimethyl thiazol-2-yl)-2,5-diphenyltetrazoliumbromide (MTT) solution was added to a medium, and the cells were further incubated for 4 hours. Subsequently, all of the medium was removed, the same volume of a dimethyl sulfoxide (DMSO) solution was added for 15 minutes to dissolve formazan. Using a UV/VIS spectrophotometer, each well of a plate was measured at 540 nm to measure relative cell viability.

Mitochondrial DNA Quantification

To quantify the copy number of mitochondrial DNA (mtDNA), by the method described in Autophagy. 2014; 10:785-802: The AMPK-PPARGC1A pathway is required for antimicrobial host defense through activation of autophagy, an mtDNA to nuclear DNA (nDNA) ratio was measured. Pyruvate kinase (Pklr) was used as a marker for nDNA and NADH dehydrogenase subunit 1 (mt-Nd1) was used as a marker for mtDNA. A real-time PCR reaction was performed according to the manufacturer's instructions (QuantiFast SYBR green PCR master mix; Qiagen, 204052), and temperature cycling was performed in QuantStudio™ 3 (ABI). The mtDNA content was normalized to a nucleic acid (DNA) content.

Measurement of Mitochondrial Membrane Potential

As described in C. S. Yang et al., Autophagy, 10(5):[0198] 785-802 (2014), the mitochondrial membrane potential (ΔΨm) of intact cells was measured with modification. Tetramethyl rhodamine, ethyl ester (TMRE; 200 nM, Molecular Probe-Invitrogen, T669) was added to a cell suspension. The cells were incubated in a dark place at 37° C. for 30 minutes. ΔΨm was measured by flow cytometry, and data was analyzed using FlowJo software. TMRE fluorescence was measured using an FLRE channel (582 nm).

Mitochondria Complex V Activity Assay

The activity of complex V was measured using a MitoTox Complex V OXPHOS Activity Microplate Assay kit manufactured by Abcam (ab109907, MA, Cambridge) according to the manufacturer's instructions. The activity of complex V was measured by monitoring the change in absorbance at 340 nm for 1 hour at 30° C. Oligomycin (Sigma, 04876) was used as a positive control for the assay.

Mouse Model Xenograft 4 to 6-week-old female athymic nude mice (Central Lab. Animal, Korea) were used for a tumor xenograft experiment (Bacillus Calmette-Guerin cell wall cytoskeleton enhances colon cancer radiosensitivity through autophagy. Autophagy. 2010; 6:46-60). Briefly, $1\times10^6$ HCT116 cells suspended in a 0.1 mL cell medium were subcutaneously injected into the animals, and observed for 7 to 10 days through tumor volume measurement. When the tumor size reached an average volume of 200 or 600 mm$^3$, treatment was initiated. The tumor volume was measured every third day using skin calipers, calculated as tumor length×tumor width$^2$×0.5 and then expressed in mm$^3$. All animals were maintained in a specific pathogen-free environment.

Statistical Analysis

All data was analyzed using a Student's t-test with Bonferroni adjustment or ANOVA for multiple comparison, and expressed as mean±SD. Statistical analysis was performed using the SPSS (Version 12.0) statistical software program (SPSS). A difference was considered significant at $p<0.05$.

[Results]

Colon Cell Death is Induced Via rGRA8-PKCα-SIRT3-ATP5A1 Pathway

PKCα-phosphorylated GRA8 is bound with mitochondrial SIRT3; SIRT3 interacts with ATP5A1 to control an acetylation state and activity. Deacetylated ATP5A1 participates in various mitochondrial processes, and SIRT3 may mediate overall changes in mitochondrial activity, which is critical for tumor growth. It was determined whether rGRA8 and its mutants cause cell death in various cancer cell lines. FIGS. 1A and 1B show that WT rGRA8 induced cell death in human colon cancer cell lines (HCT116 and HT-29) over time, but rGRA8 mutants do not. Similar to treatment in macrophages (Non-Patent Document 1), the treatment of HCT116 cells with WT rGRA8 not only significantly increased the binding of rGRA8 to ATP5A1, SIRT3 and ATP5C1 but also increased ATP5A1 deacetylation (FIG. 1C). Therefore, WT rGRA8 induces cell death in human colon cancer cells via a mitochondrial metabolic resuscitation pathway.

ATRAM-Conjugated GRA8 Peptide Designed to Target Tumors

A combined study showed that a 40-amino acid sequence (aa 183-222) or 28-amino acid sequence (aa 242-269) at the C-terminus of GRA8 is sufficient for mitochondrial targeting or ATP5A1/SIRT3 interaction (Non-Patent Document 1). Thus, the transduction domain of the HIV-1 Tat protein known as a retro-inverso peptide was added to a 9$^{th}$ to 10$^{th}$ amino acid sequence of GRA8 for intracellular delivery to prevent protein degradation, and is indicated as a Tat-GRA8 peptide (Tables 1 and 2). These peptides were tested for potential minimal residues of GRA8 for mitochondrial targeting and ATP5A1/SIRT3 interaction. Twelve hours after transfection with GST-GRA8 or in treatment with rGRA8, 293T cells or bone marrow-derived macrophages were incubated with Tat alone or other Tat-GRA8 peptides, followed by subcellular fractionation to determine the mitochondrial localization of GRA8. This showed that the Tat-GRA8 (aa 213-222) peptide can effectively block mitochondrial targeting within 6 hours of incubation, which however is impossible with only a Tat peptide (FIG. 2A). In addition, the Tat-GRA8 (aa 260-269) peptide was able to effectively prevent the GRA8-ATP5A1/SIRT3 interaction within 6 hours of incubation as determined by GST-pulldown assay for 293T cells (FIGS. 2B and 3). Therefore, such data shows the minimal region of GRA8 for mitochondria targeting and ATP5A1/SIRT3 interaction.

ATRAM strongly interacts with cancer cells under an acidic condition to emphasize excellent CTP. Therefore, to target a tumor and activate mitochondrial metabolism, an ATRAM-conjugated multifunctional GRA8 peptide was designed (FIG. 2C). To investigate the role of the ATRAM-conjugated multifunctional GRA8 peptide in cancer cells, bacterially-purified His-tagged rATRAM-GRA8-M/AS and its mutants were generated. The purified rATRAM-GRA8-M/AS (10 kDa) was confirmed by SDS-PAGE and immunoblotting (FIG. 2D). No significant cytotoxic differences in macrophages with respect to rATRAM-GRA8-M/AS and its mutants were observed, compared with a vector control (FIG. 2E). Therefore, the ATRAM-conjugated multifunctional GRA8 peptide is expected to be specific for cancer cells by regulating the mitochondrial mechanism of cancer cells.

rATRAM-GRA8-M/AS Shows Mitochondrial Activity and Biosynthesis in HCT116

Figure 4A:
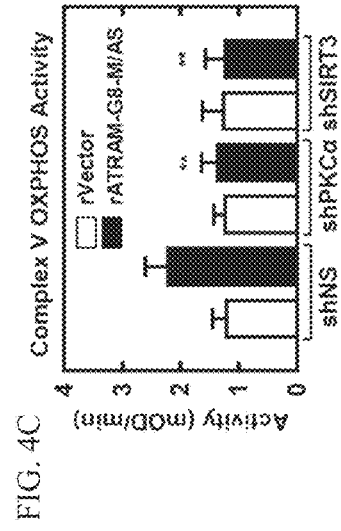
FIGS. 4A, 4B, 4C, 4D and 4E show HCT116 cell death by rATRAM-GRA8-M/AS-induced mitochondrial activation [(A and B) HCT116 cells were incubated with WT rGRA8 or rATRAM-GRA8-M/AS and its mutants for indicated times, and then cell viability was measured with an MTT assay. (C-E) HCT116 cells were transduced with lentivirus-shRNA-NS or lentivirus-shRNA-PKCα or SIRT3 (MOI=100) using polybrene (8 μg/mL) (right) for 2 days. The cells were stimulated with rATRAM-GRA8-M/AS for 1 day and subjected to enzymatic activity of OXPHOS V, and (C) MitoTracker fluorescence signals were assessed by flow cytometry. (D) A bar graph indicates a mitochondrial mass (MFI), and (E) the mtDNA content of BMDM was measured by quantitative real-time PCR. The mtDNA content was normalized by nuclear DNA. Significant differences were determined by comparison with control treatment ( P<0.01; * P<0.001). Data represents five independent experiments with similar results].
Figure 4C:
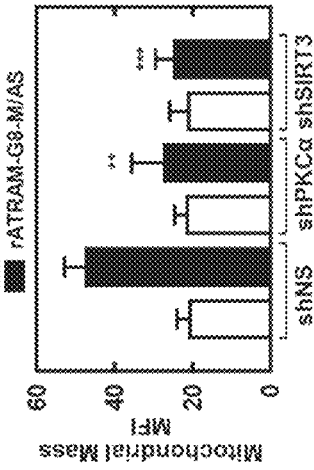
Figure 4D:
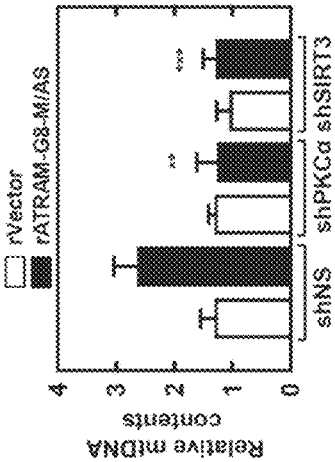
Figure 4B:
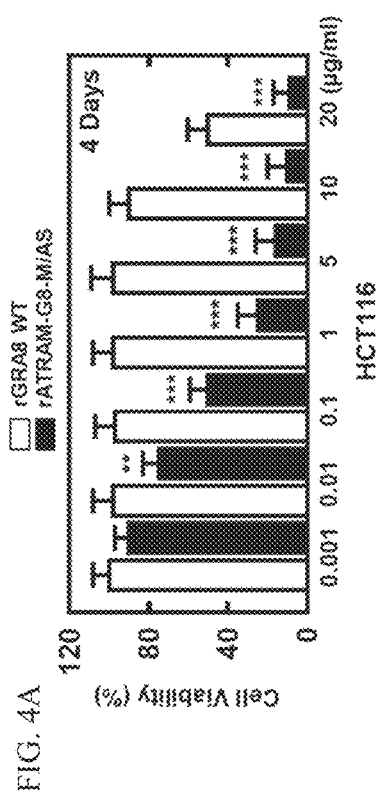
Figure 4E:
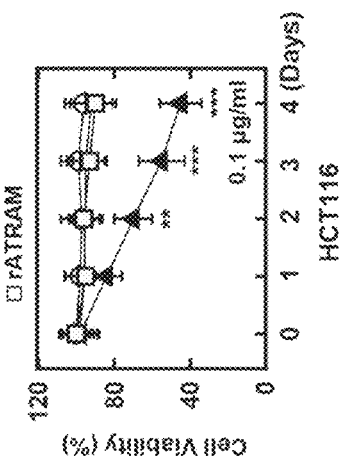

It was confirmed whether rATRAM-GRA8-M/AS has rGRA8-mimetic pharmacological and biological profiles. Consistent with the activity of rGRA8 alone, rATRAM-GRA8-M/AS induced cell death in HCT116 cells in a dose-dependent manner. Surprisingly, the IC50 of rATRAM-GRA8-M/AS was 0.1 µg/ml, which is 200-fold improved compared with that found in the case of rGRA8 alone, that is, 20 µg/ml (FIG. 4A). In addition, no significant difference in cytotoxicity was observed between rATRAMGRA8-M/AS and its mutants or the vector control in HCT116 cells (FIG. 4B). This finding indicates that GRA8 regions for mitochondrial targeting and ATP5A1/SIRT3 are essential for cancer cell death. Afterward, the mitochondrial metabolism parameters of rATRAMGRA8-M/AS were investigated. In FIGS. 4C and 4D, rATRAM-GRA8-M/AS enhanced complex V OXPHOS activity, mitochondrial mass and mitochondrial DNA content via SIRT3 and PKCα in HCT116 cells. Therefore, rATRAM-GRA8-M/AS acts as a selective and potent metabolic modulator by mitochondria-targeted metabolic resuscitation.

Antitumor Activity of rATRAM-GRA8-M/AS in HCT116 Xenografts

Figure 5A:
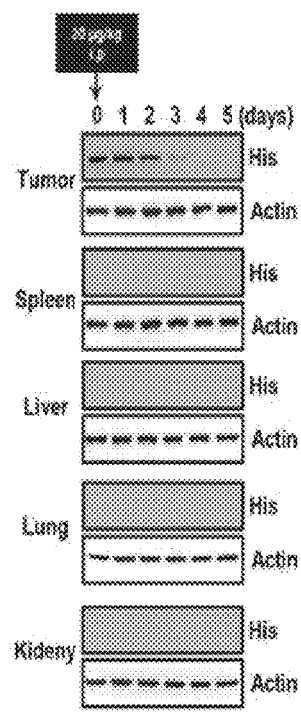
FIGS. 5A and 5B shows the pharmacokinetics and drug distribution of rATRAM-GRA8-M/AS [(A) The pharmacokinetics and pharmacokinetic distribution for rATRAM-GRA8-M/AS in tumor-bearing mice. As described in the method section, HCT116 cells were subcutaneously injected into the flank of a BALB/c mouse. The HCT116 cells were administered into the mouse by intraperitoneal injection once (left) or twice (right), and then the mouse was sacrificed on day 5. His expression was evaluated by immunoblotting (IB) in various organs from a mouse. The whole cell lysate was used for IB with anti-actin. Data represents four independent experiments with similar results. (B) The schematic diagram of an rGRA8 WT (upper)-treated xenograft model. HCT116 cells were subcutaneously injected into the flank of a nude mouse. The length and width of the tumors were measured using calipers, and a tumor volume was calculated every third day for 30 days. Individual tumor volumes from each mouse in each group were averaged and graphed over days after inoculation. Statistical significance was determined by two-way analysis of variance (ANOVA) with a Tukey's post-test; * P<0.05, *** P<0.001, compared with rVector. Each group included 10 mice. Data represents two independent experiments with similar results.

Before confirmation of the possibility of in vivo treatment, the pharmacokinetics and pharmacodistribution of rATRAMGRA8-M/AS were investigated. rATRAM-GRA8-M/AS proteins were located in tumor cells in several organs as detected by immunoblotting. This location was maintained for up to 2 days and gradually disappeared by day 3 (FIG. 5A).

The antitumor activity of rATRAM-GRA8-M/AS in xenograft mice containing HCT116 cells was confirmed. rATRAM-GRA8-M/AS (20 µg/kg, intraperitoneal injection) treatment inhibited the growth of tumors which started to initially grow (FIG. 6A) and actively growing tumors (FIG. 6B) in the mice. In addition, to evaluate potential clinical applicability, a mitochondrial target protein-binding profile and OXPHOS activity were determined to confirm the pharmacological activity of rATRAM-GRA8-M/AS in vivo.

Figure 5B:
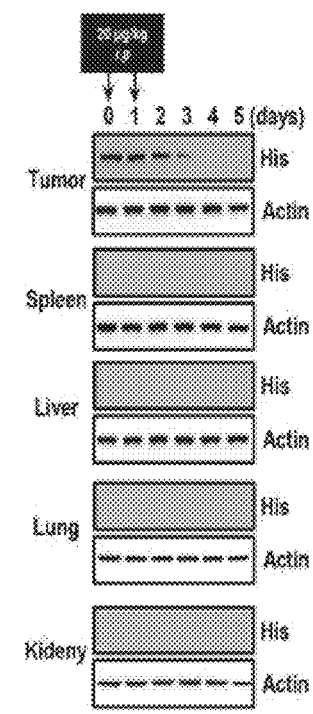
Figure 5B:
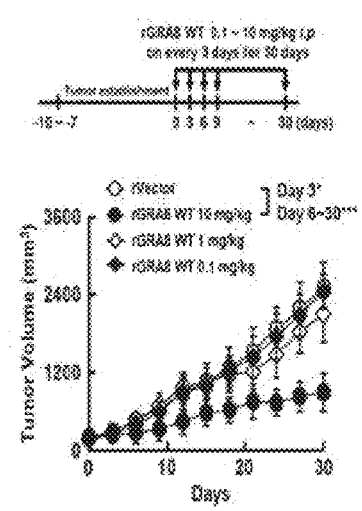

The treatment with rATRAM-GRA8-M/AS significantly increased binding of rGRA8 to ATP5A1, SIRT3 and ATP5C1. In addition, an ATP5A1 deacetylation level and a mitochondrial protein biosynthesis level were increased in tumor lysates (FIG. 6A, bottom). Surprisingly, rATRAM-GRA8-M/AS had an IC50 of 20 μg/kg, which is 500-fold improved compared with that of rGRA8 alone, that is, 10 mg/kg (FIGS. 6A and 5B).

Figure 7A:
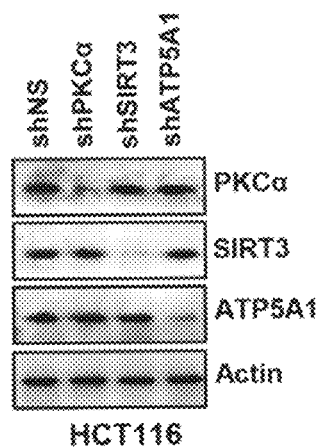
FIGS. 7A, 7B, 7C and 7D show the knockdown effect and in vivo immunogenicity of rATRAM-GRA8-M/AS in HCT 116 [(A) HCT116 cells were transduced with lentivirus-shRNA-NS or lentivirus-shRNA-PKCα, SIRT3 or ATP5A1 with polybrene (8 μg/mL) for 2 days. Immunoblotting was performed with anti-PKCα, anti-ATP5A1, anti-SIRT3 or anti-actin. Data represents five independent experiments with similar results. (B) The schematic diagram of a xenograft model treated with rVector (upper). HCT116-expressing ATP5A1 WT and mutant cells were subcutaneously injected into the flank of nude mice. Significant differences were compared with rVector. Each group included 10 mice. Data represents two independent experiments with similar results. (C) Humoral immune responses in BALB/C mice. The mice were immunized via each route (intravenous injection or intraperitoneal injection) every third day, and subjected to blood collection on day 40. A level of IgG specific for rATRAM-GRA8-M/AS or ovalbumin (OVA) was measured by ELISA. The values are expressed as mean±standard deviation for absorbance (OD) at 450 nm. Each group included five mice. (D) Cytokine response for rATRAM-GRA8-M/AS in tumor-bearing mice. As described in the method section, HCT116 cells were subcutaneously injected into the flank of a BALB/c mouse. A serum cytokine level was measured on day 30 after administration. Each group included 10 mice.
Figure 7B:
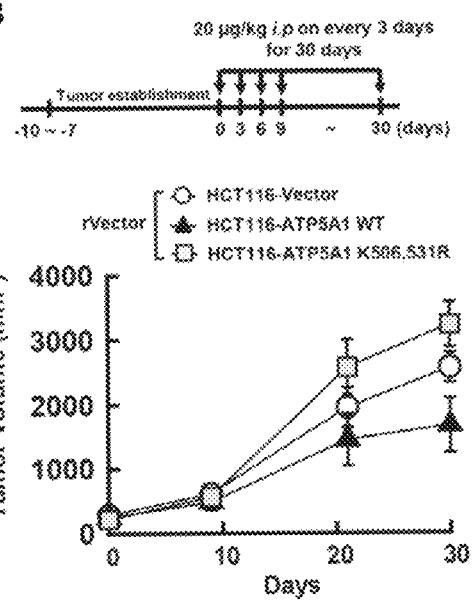

To clarify the roles of PKCα, SIRT3 and ATP5A1 in rATRAM-GRA8-M/AS-induced antitumor activity, PKCα-, SIRT3- and ATP5A1-deficient HCT116 cells were generated using specific lentiviral shRNA. Subsequently, the tumor inhibitory effects of shPKCα, shSIRT3 and shATP5A1-HCT116 cells were evaluated in rATRAM-GRA8-M/AS-treated xenograft mice. In HCT116 colon cancer xenograft models, a decrease in tumor size and delayed tumor growth by rATRAM-GRA8-M/AS were dependent on PKCα, SIRT3, ATP5A1 (FIGS. 6C-E and FIG. 7A) and the acetylation state of ATPA1 K506 and K531 (FIGS. 6F and 7B).

Figure 7C:
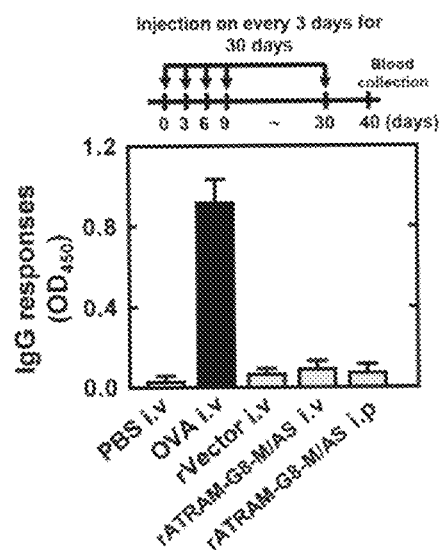
Figure 7D:
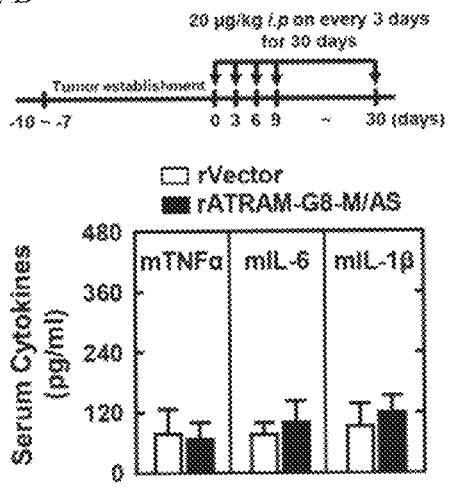

Since immunogenicity is closely related with safety and efficacy, it is one of the critical factors for development of therapeutic proteins. Therefore, by monitoring the production of antibodies against rATRAM-GRA8-M/AS in immunized mice, the immunogenicity of rATRAM-GRA8-M/AS was investigated. After three consecutive injections of rATRAM-GRA8-M/AS, a level of IgG antibody was analyzed using enzyme-linked immunosorbent assay (ELISA). Ovalbumin was used as a positive control. While the level of an antibody specific for rATRAM-GRA8-M/AS is negligible, ovalbumin induced a significant increase in antibody level (FIG. 7C). In addition, rATRAM-GRA8-M/AS induced negligible production of inflammatory cytokines in tumor-bearing mice. Serum TNF-α, IL-6 and IL-1β levels in BALB/c mice were almost similar to that of the negative control (FIG. 7D), and it showed that rATRAM-GRA8-M/AS causes negligible immunogenicity and immune responses. Therefore, rATRAM-GRA8-M/AS is a biocompatible biomaterial, and rATRAM-GRA8-M/AS-mediated mitochondrial metabolic resuscitation is critical for antitumor activity.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A *Taxoplasma gondii* GRAS-derived recombinant peptide, which is represented by SEQ ID NO: 1.

2. A gene which encodes the peptide of claim 1 and is represented by SEQ ID NO: 5.

3. A recombinant expression vector comprising the gene of claim 2.

4. A pharmaceutical composition for treating coloretal cancer, comprising a *Toxoplasma gondii* GRA8-derived recombinant peptide represented by SEQ ID NO: 1 as an active ingredient.

5. A functional food for improving colorectal cancer, comprising a *Toxoplasma gondii* GRA8-derived recombinant peptide represented by SEQ ID NO: 1.

6. A method of treating colorectal cancer, comprising:
   administering the pharmaceutical composition of claim 4 to a subject who already has colorectal cancer.

7. A method of treating colorectal cancer, comprising administering a therapeutically effective amount of a *Toxoplasma gondii* GRAS-derived recombinant peptide represented by SEQ ID NO: 1 to a subject.

* * * * *

UNITED STATES PATENT AND TRADEMARK OFFICE
CERTIFICATE OF CORRECTION

PATENT NO. : 11,492,376 B2
APPLICATION NO. : 17/130475
DATED : November 8, 2022
INVENTOR(S) : Chul-Su Yang et al.

Page 1 of 1

It is certified that error appears in the above-identified patent and that said Letters Patent is hereby corrected as shown below:

On the Title Page

In item (73) Assignee:
"Industry-University Cooperation Foundation Ranyang University Erica Campus, Incheon (KR)"
Should be changed to:
-- Industry-University Cooperation Foundation Hanyang University Erica Campus, Ansan-si (KR) --

Signed and Sealed this
Fourteenth Day of March, 2023

Katherine Kelly Vidal
*Director of the United States Patent and Trademark Office*

SEQUENCE LISTING

```
<160> NUMBER OF SEQ ID NOS: 18

<210> SEQ ID NO 1
<211> LENGTH: 92
<212> TYPE: PRT
<213> ORGANISM: Artificial Sequence
<220> FEATURE:
<223> OTHER INFORMATION: rATRAM-G8-M/AS

<400> SEQUENCE: 1

Gly Leu Ala Gly Leu Ala Gly Leu Leu Gly Leu Glu Gly Leu Leu Gly
1               5                   10                  15

Leu Pro Leu Gly Leu Leu Glu Gly Leu Trp Leu Gly Leu Glu Leu Glu
                20                  25                  30

Gly Asn Gly Leu Ala Gly Leu Ala Gly Leu Leu Gly Leu Glu Gly Leu
            35                  40                  45

Leu Gly Leu Pro Leu Gly Leu Leu Glu Gly Leu Trp Leu Gly Leu Glu
    50                  55                  60

Leu Glu Gly Asn Gly Gly Ala Thr Ala Thr Thr Thr Thr Thr Thr Arg
65                  70                  75                  80

Gly Gly Tyr Arg Phe Thr Val Gln Thr Thr Gln Asn
                85                  90

<210> SEQ ID NO 2
<211> LENGTH: 80
<212> TYPE: PRT
<213> ORGANISM: Artificial Sequence
<220> FEATURE:
<223> OTHER INFORMATION: ATRAM-G8-M

<400> SEQUENCE: 2

Gly Leu Ala Gly Leu Ala Gly Leu Leu Gly Leu Glu Gly Leu Leu Gly
1               5                   10                  15

Leu Pro Leu Gly Leu Leu Glu Gly Leu Trp Leu Gly Leu Glu Leu Glu
                20                  25                  30

Gly Asn Gly Leu Ala Gly Leu Ala Gly Leu Leu Gly Leu Glu Gly Leu
            35                  40                  45
```

```
Leu Gly Leu Pro Leu Gly Leu Leu Glu Gly Leu Trp Leu Gly Leu Glu
 50                  55                  60
Leu Glu Gly Asn Gly Gly Ala Thr Ala Thr Thr Thr Thr Thr Thr Arg
 65                  70                  75                  80

<210> SEQ ID NO 3
<211> LENGTH: 68
<212> TYPE: PRT
<213> ORGANISM: Artificial Sequence
<220> FEATURE:
<223> OTHER INFORMATION: ATRAM-ATRAM

<400> SEQUENCE: 3

Gly Leu Ala Gly Leu Ala Gly Leu Leu Gly Leu Glu Gly Leu Leu Gly
 1               5                  10                  15
Leu Pro Leu Gly Leu Leu Glu Gly Leu Trp Leu Gly Leu Glu Leu Glu
                 20                  25                  30
Gly Asn Gly Leu Ala Gly Leu Ala Gly Leu Leu Gly Leu Glu Gly Leu
                 35                  40                  45
Leu Gly Leu Pro Leu Gly Leu Leu Glu Gly Leu Trp Leu Gly Leu Glu
 50                  55                  60
Leu Glu Gly Asn
 65

<210> SEQ ID NO 4
<211> LENGTH: 269
<212> TYPE: PRT
<213> ORGANISM: Toxoplasma gondii

<400> SEQUENCE: 4

Met Ala Leu Pro Leu Arg Val Ser Ala Thr Val Phe Val Val Phe Ala
 1               5                  10                  15
Val Phe Gly Val Ala Arg Ala Met Asn Gly Pro Leu Ser Tyr His Pro
                 20                  25                  30
Ser Ser Tyr Gly Ala Ser Tyr Pro Asn Pro Ser Asn Pro Leu His Gly
                 35                  40                  45
Met Pro Lys Pro Glu Asn Pro Val Arg Pro Pro Pro Gly Phe His
 50                  55                  60
Pro Ser Val Ile Pro Asn Pro Pro Tyr Pro Leu Gly Thr Pro Ala Gly
 65                  70                  75                  80
Met Pro Gln Pro Glu Val Pro Pro Leu Gln His Pro Pro Pro Thr Gly
                 85                  90                  95
Ser Pro Pro Ala Ala Ala Pro Gln Pro Pro Tyr Pro Val Gly Thr Pro
                 100                 105                 110
Gly Met Pro Gln Pro Glu Ile Pro Pro Val His Arg Pro Pro Pro
                 115                 120                 125
Gly Phe Arg Pro Glu Val Ala Pro Val Pro Pro Tyr Pro Val Gly Thr
                 130                 135                 140
Pro Thr Gly Met Pro Gln Pro Glu Ile Pro Ala Val His His Pro Phe
 145                 150                 155                 160
Pro Tyr Val Thr Thr Thr Thr Ala Ala Pro Arg Val Leu Val Tyr
                 165                 170                 175
Lys Ile Pro Tyr Gly Gly Ala Ala Pro Arg Ala Pro Val Pro
                 180                 185                 190
Pro Arg Met Gly Pro Ser Asp Ile Ser Thr His Val Arg Gly Ala Ile
                 195                 200                 205
Arg Arg Gln Pro Ala Thr Ala Thr Thr Thr Thr Thr Arg Asn Val
```

```
            210                 215                 220
Leu Leu Arg Thr Ala Ile Leu Ala Ala Ala Ala Thr Leu Ile Ala
225                 230                 235                 240

Leu Phe Arg Gln Arg Pro Leu Phe Thr Glu Gly Val Arg Met Phe Pro
                245                 250                 255

Asp Phe Gln Tyr Arg Phe Thr Val Gln Thr Thr Gln Asn
            260                 265

<210> SEQ ID NO 5
<211> LENGTH: 276
<212> TYPE: DNA
<213> ORGANISM: Artificial Sequence
<220> FEATURE:
<223> OTHER INFORMATION: rATRAM-G8-M/AS

<400> SEQUENCE: 5
ggcctggccg gcctggccgg cctgctgggc ctggaaggcc tgccgggcct gcccctgggc      60
ctgctggaag gcctgtggct gggcctggaa ctggaaggaa acggcctggc cggcctggcc     120
ggcctgctgg gcctggaagg cctgccgggc ctgcccctgg gcctgctgga aggcctgtgg     180
ctgggcctgg aactggaagg aaacgggggg gctaccgcca ccacaaccac tactacccgc     240
ggggggagat tcaccgtcca aacgacgcag aattaa                              276

<210> SEQ ID NO 6
<211> LENGTH: 34
<212> TYPE: PRT
<213> ORGANISM: Artificial Sequence
<220> FEATURE:
<223> OTHER INFORMATION: ATRAM

<400> SEQUENCE: 6

Gly Leu Ala Gly Leu Ala Gly Leu Leu Gly Leu Glu Gly Leu Leu Gly
1               5                   10                  15

Leu Pro Leu Gly Leu Leu Glu Gly Leu Trp Leu Gly Leu Glu Leu Glu
            20                  25                  30

Gly Asn

<210> SEQ ID NO 7
<211> LENGTH: 10
<212> TYPE: PRT
<213> ORGANISM: Artificial Sequence
<220> FEATURE:
<223> OTHER INFORMATION: a mitochondrial targeting sequence

<400> SEQUENCE: 7

Ala Thr Ala Thr Thr Thr Thr Thr Thr Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: ATP5A1/SIRT3 binding sequence

<400> SEQUENCE: 8

Tyr Arg Phe Thr Val Gln Thr Thr Gln Asn
1               5                   10

<210> SEQ ID NO 9
<211> LENGTH: 10
<212> TYPE: PRT
```

<213> ORGANISM: Artificial Sequence
<220> FEATURE:
<223> OTHER INFORMATION: Tat

<400> SEQUENCE: 9

Gly Arg Lys Lys Arg Arg Gln Arg Arg Arg
1               5                   10

<210> SEQ ID NO 10
<211> LENGTH: 51
<212> TYPE: PRT
<213> ORGANISM: Artificial Sequence
<220> FEATURE:
<223> OTHER INFORMATION: Tat-GRA8-(183-222)

<400> SEQUENCE: 10

Gly Arg Lys Lys Arg Arg Gln Arg Arg Arg Gly Ala Ala Pro Pro Arg
1               5                   10                  15

Ala Pro Pro Val Pro Pro Arg Met Gly Pro Ser Asp Ile Ser Thr His
                20                  25                  30

Val Arg Gly Ala Ile Arg Arg Gln Pro Ala Thr Ala Thr Thr Thr Thr
            35                  40                  45

Thr Thr Arg
    50

<210> SEQ ID NO 11
<211> LENGTH: 21
<212> TYPE: PRT
<213> ORGANISM: Artificial Sequence
<220> FEATURE:
<223> OTHER INFORMATION: Tat-GRA8-(183-192)

<400> SEQUENCE: 11

Gly Arg Lys Lys Arg Arg Gln Arg Arg Arg Gly Ala Ala Pro Pro Arg
1               5                   10                  15

Ala Pro Pro Val Pro
                20

<210> SEQ ID NO 12
<211> LENGTH: 21
<212> TYPE: PRT
<213> ORGANISM: Artificial Sequence
<220> FEATURE:
<223> OTHER INFORMATION: Tat-GRA8-(193-202)

<400> SEQUENCE: 12

Gly Arg Lys Lys Arg Arg Gln Arg Arg Arg Gly Pro Arg Met Gly Pro
1               5                   10                  15

Ser Asp Ile Ser Thr
                20

<210> SEQ ID NO 13
<211> LENGTH: 21
<212> TYPE: PRT
<213> ORGANISM: Artificial Sequence
<220> FEATURE:
<223> OTHER INFORMATION: Tat-GRA8-(203-212)

<400> SEQUENCE: 13

Gly Arg Lys Lys Arg Arg Gln Arg Arg Arg Gly His Val Arg Gly Ala
1               5                   10                  15

Ile Arg Arg Gln Pro
                20

<210> SEQ ID NO 14
<211> LENGTH: 21
<212> TYPE: PRT
<213> ORGANISM: Artificial Sequence
<220> FEATURE:
<223> OTHER INFORMATION: Tat-GRA8-(213-222)

<400> SEQUENCE: 14

Gly Arg Lys Lys Arg Arg Gln Arg Arg Gly Ala Thr Ala Thr Thr
1               5                   10                  15

Thr Thr Thr Thr Arg
            20

<210> SEQ ID NO 15
<211> LENGTH: 39
<212> TYPE: PRT
<213> ORGANISM: Artificial Sequence
<220> FEATURE:
<223> OTHER INFORMATION: Tat-GRA8-(242-269)

<400> SEQUENCE: 15

Gly Arg Lys Lys Arg Arg Gln Arg Arg Gly Phe Arg Gln Arg Pro
1               5                   10                  15

Leu Phe Thr Glu Gly Val Arg Met Phe Pro Asp Phe Gln Tyr Arg Phe
            20                  25                  30

Thr Val Gln Thr Thr Gln Asn
        35

<210> SEQ ID NO 16
<211> LENGTH: 20
<212> TYPE: PRT
<213> ORGANISM: Artificial Sequence
<220> FEATURE:
<223> OTHER INFORMATION: Tat-GRA8-(242-250)

<400> SEQUENCE: 16

Gly Arg Lys Lys Arg Arg Gln Arg Arg Gly Phe Arg Gln Arg Pro
1               5                   10                  15

Leu Phe Thr Glu
            20

<210> SEQ ID NO 17
<211> LENGTH: 20
<212> TYPE: PRT
<213> ORGANISM: Artificial Sequence
<220> FEATURE:
<223> OTHER INFORMATION: Tat-GRA8-(251-259)

<400> SEQUENCE: 17

Gly Arg Lys Lys Arg Arg Gln Arg Arg Gly Gly Val Arg Met Phe
1               5                   10                  15

Pro Asp Phe Gln
            20

<210> SEQ ID NO 18
<211> LENGTH: 21
<212> TYPE: PRT
<213> ORGANISM: Artificial Sequence
<220> FEATURE:
<223> OTHER INFORMATION: Tat-GRA8-(260-269)

```
<400> SEQUENCE: 18

Gly Arg Lys Lys Arg Arg Gln Arg Arg Arg Gly Tyr Arg Phe Thr Val
1               5                   10                  15

Gln Thr Thr Gln Asn
            20
```